United States Patent

DiFilippo et al.

[11] Patent Number: 5,813,983
[45] Date of Patent: Sep. 29, 1998

[54] DEPTH-OF-INTERACTION AND OTHER HIGH ORDER MOMENTS FILTERING FOR IMPROVED DETECTION IN THICK SCINTILLATION CRYSTALS

[75] Inventors: Frank P. DiFilippo; Daniel Gagnon, both of Mayfield Heights, Ohio

[73] Assignee: Picker International, Inc., Highland Heights, Ohio

[21] Appl. No.: 867,737

[22] Filed: Jun. 3, 1997

[51] Int. Cl.$^6$ ..................................................... A61B 6/00
[52] U.S. Cl. ................... 600/407; 600/436; 250/363.02; 250/363.03; 250/369
[58] Field of Search ................................... 600/407, 436; 250/363.01–363.03, 363.07, 363.1, 366, 369

[56] References Cited

U.S. PATENT DOCUMENTS 5,122,667  6/1992  Thompson .......................... 250/363.03
5,576,546  11/1996  Gagnon .................................. 250/369

OTHER PUBLICATIONS

"Maximum Likelihood Positioning in the Scintillation Camera Using Depth of Interaction" Gagnon, IEEE Trans. on Med. Imaging, vol. 12 No. 1 Mar. 1993.

"Storage–Phosphor–Based Digital Mammography using a Low–Dose X–Ray System Optimized for Screen–Film Mammography", Jennings, et al. SPIE Vo. 2708 Feb. 1996.

*Primary Examiner*—Ruth S. Smith
*Attorney, Agent, or Firm*—Timothy B. Gurin; John J. Fry

[57] ABSTRACT

Radiation from a subject (18) which is received by a scintillation crystal (12) interacts with the scintillation crystal to produce a burst of scintillation light photons. The depth distribution at which the interaction occurs varies in accordance with the energy of the received radiation. Low-energy radiation tends to interact at a shallow depth relative to a front face of the scintillation crystal and radiation with a high energy tends to interact relatively deeply into the crystal. A moment processor (20) processes electronic information from photomultiplier tubes (14) which view the scintillation crystal to generate zero-th moment or energy information, first moment or coordinate information and second moment or depth information. The event information is filtered (34, 62, 66, 82) in accordance with depth (26), e.g., sorted into acceptable/unacceptable information, information corresponding to each of two or more energies of radiation, and the like.

19 Claims, 3 Drawing Sheets

DEPTH-OF-INTERACTION AND OTHER HIGH ORDER MOMENTS FILTERING FOR IMPROVED DETECTION IN THICK SCINTILLATION CRYSTALS

BACKGROUND OF THE INVENTION

The present invention relates to the nuclear or scintillation camera art.

In nuclear cameras, a scintillation crystal receives radiation emitted from the subject and converts the radiation into a flash of light or scintillation. An array of photomultiplier tubes mounted adjacent the rear face of the scintillation crystal respond to each scintillation generating interaction and provides output electrical information relative to the coordinate position of the scintillation interaction and its energy.

In a traditional Anger-type nuclear camera, a collimator is positioned on the radiation receiving face of the scintillation crystal to restrict the paths along which the radiation can strike the scintillation crystal. In this manner, each scintillation also identifies a trajectory of the ray traversed by the radiation. From this ray information, a two-dimensional projection or three-dimensional image of the distribution of radiation sources within the subject is reconstructed with conventional reconstruction algorithms.

In positron emission tomography (PET), a multiplicity of BGO scintillation crystals and photomultiplier tubes are disposed in an array surrounding the subject. Each positron annihilation event causes a pair of radiation photons which travel along directly opposite trajectories. When a pair of scintillations occur simultaneously on two scintillation crystals, i.e., a coincident radiation event, the location of the two scintillations define the end points of the ray travelled by the radiation. In this manner, using the coincidence information and the location and magnitude of the coincident scintillation events, a series of rays are again generated. Using conventional reconstruction algorithms, the series of rays are again reconstructed into a representation of the radiation source distribution within the subject.

Positron annihilation radiation has a relatively high energy, about 511 keV. Higher energy radiation tends to pass through a thin NaI(Tl) scintillation crystal (typically 10 mm) without causing a scintillation event. Generally, thicker NaI(Tl) scintillation crystals, e.g., about 20 mm, are used to provide sufficient stopping power to convert a sufficient fraction substantially all of the higher energy positron emission radiation into scintillations.

Again, the photomultiplier tubes and electronic circuit determine the coordinate position of each scintillation relative to the plane of the scintillation crystal and each scintillation's intensity or energy. Generally, a glass light pipe is coupled between the tubes and the scintillation crystal to help spread the light between tubes to improve positioning. As the thickness of the scintillation crystal increases, the degree of uncertainty as to the exact location of the scintillation event, i.e., the depth within the crystal, increases. In general, the photomultiplier tubes respond to each scintillation with a two-dimensional generally bell-shaped curve with the apex marking the coordinate location and the area under the curve denoting the energy. It has been found that when the scintillation event occurs on the radiation receiving face, i.e., the face furthest from the photomultiplier tubes, the curve is relatively shallow and wide; whereas, when the scintillation event occurs on the rear face of the scintillation crystal closest to the photomultiplier tube plane, the curve is more sharply peaked and narrower. Thus, the width or diffusity of the response provides an indication of the depth within the scintillation crystal at which the scintillation event occurred. Stated in terms of moments, the zero-th order moment of this distribution indicates the energy of the radiation, the first moments indicate the coordinate positions of the apex of the curve, and the second order moment indicates the diffusity of the curve, hence the depth-of-interaction. As elaborated in U.S. Pat. No. 5,576,546 of Daniel Gagnon, this depth-of-interaction information can be used in various data correction techniques to improve the resultant images.

The present application provides new and unexpected uses and techniques for using the depth-of-interaction information in conventional Anger cameras, positron emission tomography, dual isotope imaging, and the like.

SUMMARY OF THE INVENTION

In accordance with one aspect of the present invention, a method of diagnostic imaging is provided. Radiation from a subject interacts with a scintillation crystal and is converted into bursts of photons of light. The light is converted into corresponding electronic data. The electronic data are reconstructed into at least one image representation. The electronic data are filtered in accordance with a depth within the scintillation crystal at which the radiation interacted with the crystal and was converted into the photon of light.

In accordance with another aspect of the present invention, a diagnostic imaging apparatus is provided. At least one detector head includes a scintillation crystal having a front face and a rear face. Radiation which is received by the scintillation crystal interacts with the crystal to generate a scintillation of light. Each scintillation is generated at a depth-of-interaction measured relative to the crystal faces. Opto-electrical converters are disposed adjacent an inner face of the crystal for converting the scintillations into electrical signals. A coordinate circuit determines a coordinate on a plane parallel to the crystal faces at which each interaction occurs. A depth circuit determines a depth at which each interaction occurs. A filter circuit selectively filters the coordinate signals from the coordinate circuit in accordance with the depth determined by the depth circuit. An image reconstruction system reconstructs the coordinates into an electronic image representation.

One advantage of the present invention is that it electronically selects the effective thickness of scintillation crystals.

Another advantage of the present invention is that it permits a scintillation crystal of a single physical thickness to have its effective thickness adjusted in an energy-dependent method.

Another advantage of the present invention resides in its improved energy level discrimination and its improved elimination of potential artifacts.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
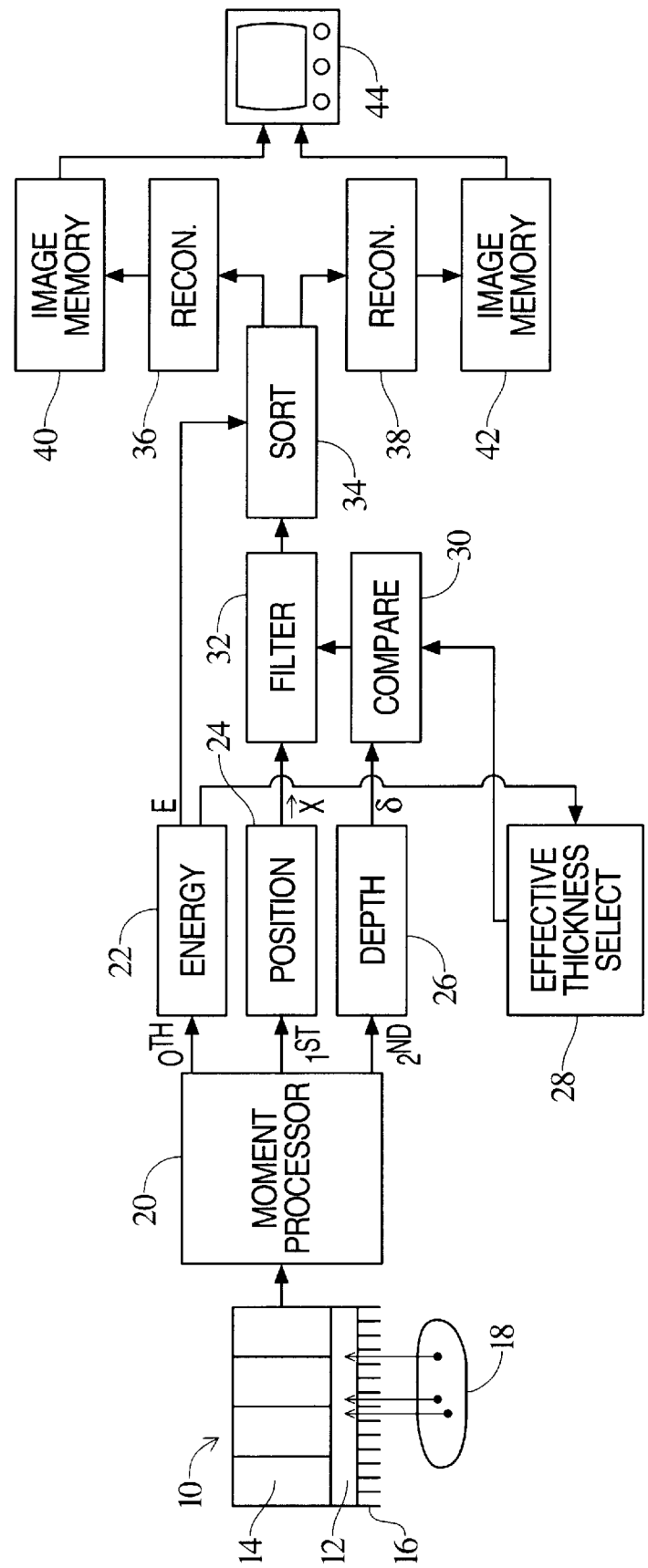
FIG. 1 is a diagrammatic illustration of a dual isotope nuclear camera in accordance with the present invention.

A nuclear camera head 10 includes a relatively thick, e.g., 20 mm, scintillation crystal 12 whose back surface is viewed by a close-packed array of photomultiplier tubes 14. A collimator 16 is mounted adjacent a front face of the scintillation crystal such that radiation from a subject 18 is collimated to pass along restricted rays through vanes of the collimator in order to reach the scintillation crystal and interact in a scintillation event.

A moment processor 20 calculates the zero-th, first, and second moments of the signals output by the photomultiplier tubes. The zero-th moment represents energy, the first moment represents coordinate position of the scintillation event generating interaction relative to a detector plane, and the second moment represents the spread of the peak, hence the depth in the scintillation crystal at which the interaction occurred. An energy circuit 22 converts the zero-th moment into a measurement of energy which is compared with the energy of the isotopes being imaged. A coordinate circuit 24 converts the first moment into x,y-coordinate positions. A depth circuit 26 converts the second moment into an indication of depth-of-interaction relative to the front face of the crystal. The depth-of-interaction information is used to filter the coordinate information, deciding whether to reject the event or to accept and continue with processing.

An effective depth selection circuit 28 is controlled by the operator to select a thickness and location of a slab of the scintillation crystal which is to be utilized. For example, the operator can select the 8 mm of the crystal closest to the front face to be the active region such that the output is substantially the same as the output from the detector head with a thin, 8 mm scintillation crystal. This would improve the resolution of the detector; since the sizes of the light pulses are more consistent, the calibration of the energy and position-determining circuits is more consistent, thus reducing the variance in the energy and position. Such a selection is appropriate for low energy isotopes, which interact primarily near the front surface of the crystal. For a slightly higher energy isotope, the operator may choose to select an intermediate slab of the scintillation crystal. For example, if the selected isotope has a penetrating power such that the median radiation photon is stopped at 8 mm into the crystal, a slab from 0–11 mm from the front face might be selected as the active region. As yet another option, if the isotope is a high energy isotope in which the maximum stopping power of the crystal is wanted, the operator might select the 0–20 mm, i.e., the entire crystal from the front face region to be the active region.

In a preferred embodiment, the depth-of-interaction filter includes a depth comparing circuit 30 which compares the calculated depth from the depth circuit 26 with the selected effective active slab of the scintillation crystal from the effective thickness circuit 28. Since the desired active thickness could depend on the event energy, the energy can be used to specify the thickness on an event-by-event basis. If the scintillation event comes from the selected slab, then the comparing circuit 30 causes an accept/reject circuit 32 to accept the event and pass the coordinate and energy values identifying the location of the event from the coordinate circuit 24. If the scintillation event is from a layer of the scintillation crystal outside of the selected slab, the accept/reject circuit discards the coordinate information. Other filter functions can, of course, be selected.

For a dual isotope imaging, isotopes with two different energy peaks are injected into the subject or isotope of one energy is injected into the subject and radiation of a second energy is transmitted through the subject. A sorting circuit 34 is controlled by the energy circuit 22 to sort the accepted coordinate values between a first isotope reconstruction system 36 and a second isotope reconstruction system 38 in accordance with the energy or zero-th moment of the event. The first and second isotope reconstruction systems can share a common reconstruction processor. The first and second image reconstruction circuits reconstruct the coordinate information into first and second isotope electronic image representations for corresponding first and second image memories 40, 42. The image reconstruction can be a projection image reconstruction, a volume image reconstruction, or other known image formats. For volume images, the detector head 10 is typically rotated around the subject. One or more displays 44 display the reconstructed images individually or in combination with each other. This procedure could be extended to more than two isotopes, or to two or more energies for the same isotope.

Figure 2:
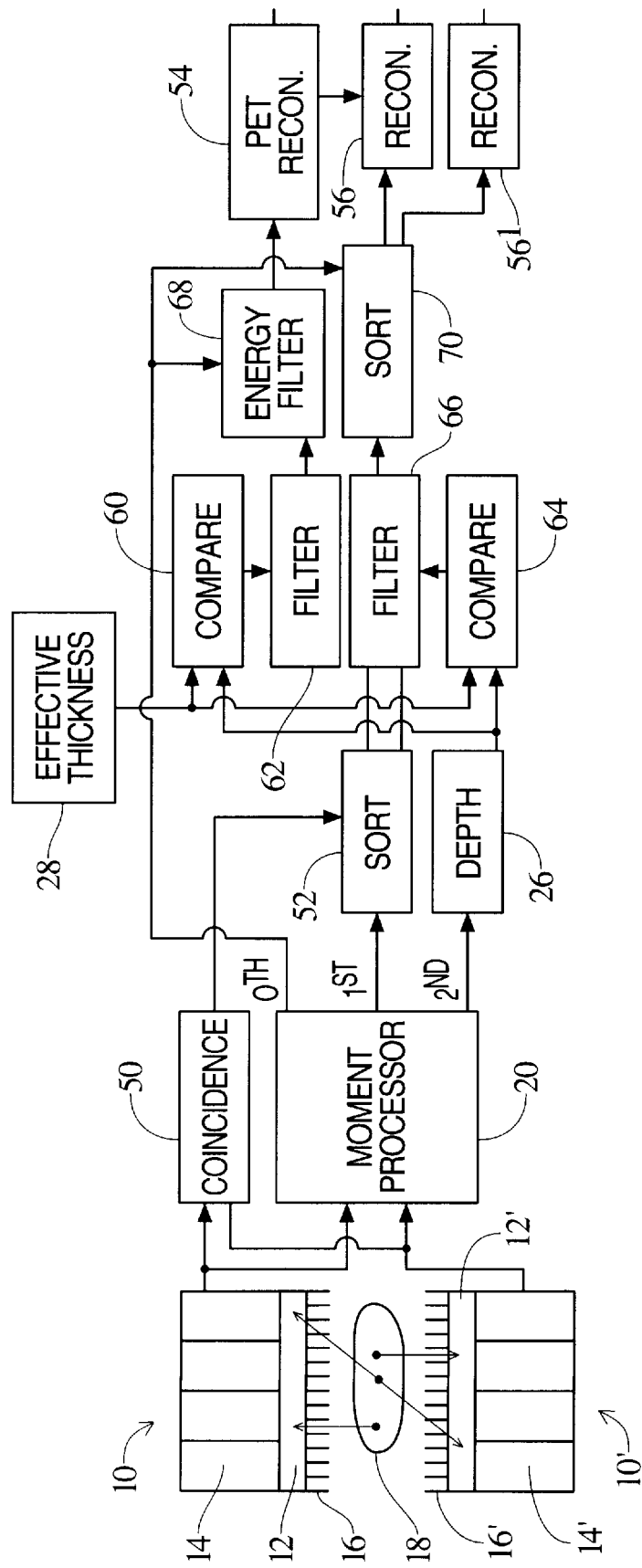
FIG. 2 is a diagrammatic illustration of a positron and low energy isotope nuclear camera in accordance with the present invention; and, FIG. 3 is another embodiment of a positron and low energy isotope nuclear camera in accordance with the present invention.

With reference to FIG. 2, a pair of like detector heads 10 and 10' of the construction discussed in conjunction with FIG. 1 are mounted on opposite sides of the subject 18 with their front faces parallel to each other. The collimators 16, 16' are selected of a material with a relatively low stopping power such that they collimate the low energy isotope and are substantially invisible to higher energy positron emission radiation. A moment processor 20 again calculates the zero-th, first, and second moments of each scintillation event. A coincidence circuit 50 determines when scintillation events occur simultaneously in both scintillation crystals. This is typically done by establishing a time window logic circuit of 22 ms or less. The coincidence circuit controls a sorting circuit 52 which sorts the coordinate pairs which occur simultaneously to a positron emission tomography reconstruction processor 54 and the coordinates of events which occur non-simultaneously to a conventional low energy reconstruction processor 56.

A depth calculating circuit 26 calculates the depth of each scintillation event within the scintillation crystals. The operator uses an effective thickness selection circuit 28 to select the slabs or layers of the scintillation crystal which are to contribute to the positron emission tomographic image and the portion of the crystal whose scintillations are to contribute the low energy image reconstruction. Typical segmentations of a 20 mm scintillation crystal might include limiting the positron emission image to scintillations between 0–20 mm from the front face of the crystal and the low energy image to scintillations in the 0–10 mm portion depth of the crystal. Another use of higher-order moments filtering is to reject multiple interaction events. Higher energy events, such as positron annihilation events, often interact by partially depositing energy at one location (Compton scattering) and depositing the remaining energy at a second location (photoelectric absorption). The calculated position is therefore an average of the two and less accurate. These events can be determined with a second or higher moment and rejected in order to improve the spatial resolution.

A comparing circuit 60 compares the selected depth for the positron emission tomographic image with the depth calculated by circuit 26 and causes a filter circuit 62 to accept or reject the coordinate pairs for the positron emission in accordance with the depth in the crystal at which the scintillation interaction occurred. Analogously, a comparing circuit 64 compares the selected depth for the low energy scintillation events with the actual depth from the depth circuit 26 and causes a filter circuit 66 to accept or reject low energy events in accordance with the depth within the scintillation crystal at which the scintillation interaction occurred.

Optionally, an energy based filter circuit 68 can be utilized to accept or reject the coordinate information in accordance with the energy of the scintillation events. Typically, such an accept/reject would window the energy at around the 511 keV and over the lower energy range of Compton scattered positrons. A similar filter circuit can be used for the scintillations attributable to the low energy radiation. Moreover, two or more low energy isotopes can be utilized. With two or more low energy isotopes, the zero-th moment controls a sorting circuit 70 which sorts the low energy radiation coordinates between reconstruction processor systems 56, 56' or discards the information in accordance with the energy levels.

This functionality is particularly important for multi-isotope imaging because the lower energy window is contaminated by scatter and partial interaction of the higher energy isotope. The high energy contamination is deeper into the crystal. This could cause inaccuracies in the positioning which could cause artifacts in the reconstructed image. This problem would be alleviated by rejecting the deeper events by higher-order moment filtering.

Figure 3:
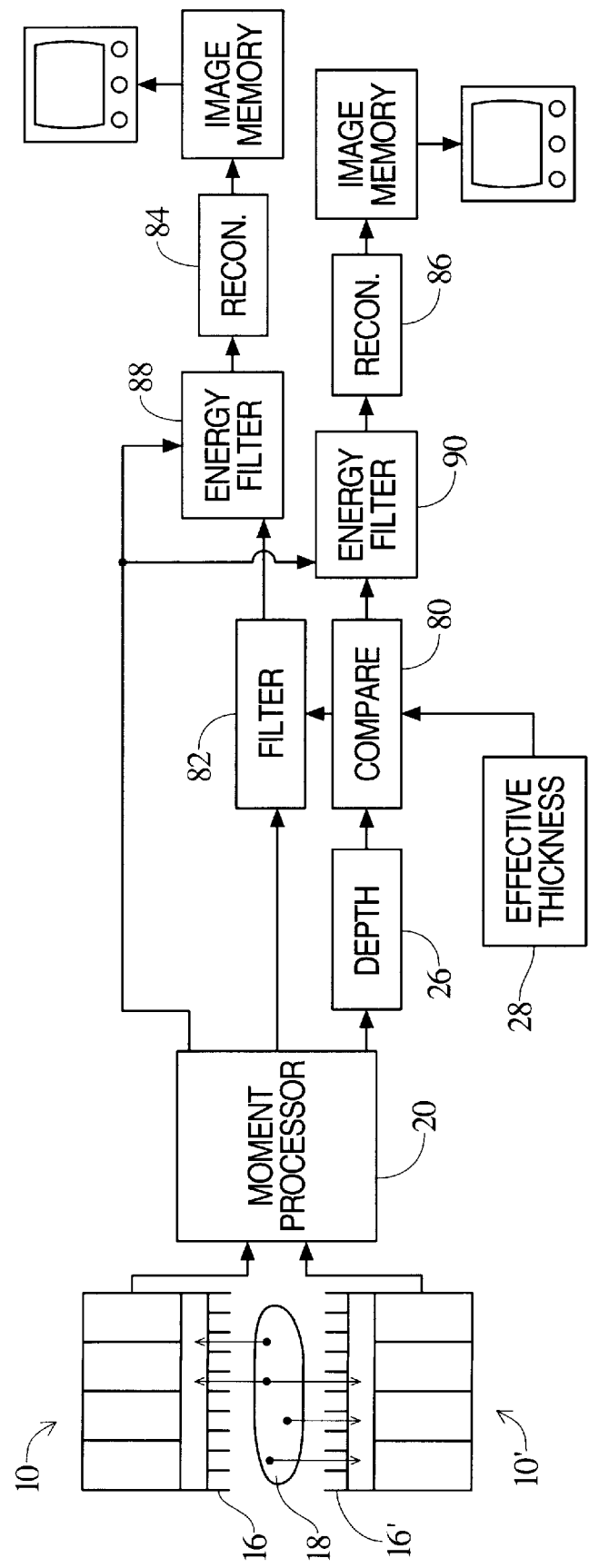

With reference to FIG. 3, a pair of detector heads 10, 10' are again mounted on opposite sides of the subject 18 with their energy receiving faces parallel to each other. The collimators 16, 16' are constructed of a material with high absorbing power such that even high energy radiation such as positron emissions are collimated. A moment processor 20 again calculates the zero-th, first, and second moments. A depth circuit converts the second moment into an indication of depth of each scintillation event. The operator uses an effective thickness selection circuit 28 to select the depth for scintillations corresponding to the positron emission energy range, e.g., 20 mm, and the depth corresponding to a low energy isotope, e.g., 0–8 mm. A comparing circuit 80 causes a filter or sorting circuit 82 to sort the first moment coordinates of each radiation interaction in accordance with the depth at which each occurred. Interactions occurring in the deep part of the crystal, e.g., the 0–20 mm range, are sent to the positron emission tomography reconstruction processor 84. Interactions occurring in the front portion of the crystal, e.g., the 0–8 mm range, are conveyed to the low energy image reconstruction processor 86. Optionally, the zero-th moment can be used to control filters 88, 90 for discarding radiation which is clearly outside the energy range of either the positron emission radiation, Compton scattered positrons, or the low energy radiation.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of diagnostic imaging comprising:
   utilizing a detector having a scintillation crystal to detect radiation from a subject, said radiation interacting with the scintillation crystal and being converted into photons of light;
   converting the photons of light into corresponding electronic data, which electronic data includes a coordinate of the interaction;
   filtering the electronic data in accordance with a depth within the scintillation crystal at which the radiation interacted with the crystal and was converted into the photons of light;
   utilizing the filtered data to reconstruct an image indicative of the detected radiation.

2. The method as set forth in claim 1, further including determining the depth from a second or higher order moment calculation on the electronic data.

3. The method as set forth in claim 1 wherein in the filtering step, photons of light from a selected slab of the crystal are accepted for reconstruction into the image representation and photons of light from outside of the selected slab are rejected.

4. The method as set forth in claim 1 wherein in the filtering step, photons of light from a first slab of the crystal are sorted for reconstruction into a first image representation and photons of light from a second slab of the crystal are sorted for reconstruction into a second image representation.

5. The method as set forth in claim 4 wherein the first and second slabs overlap.

6. The method as set forth in claim 1 further including determining at least first and second moments of the electronic data converted from each photon of light, the first moments being reconstructed into the image representation and the second moments being converted into an indication of depth within the scintillation crystal of each photon of light producing interaction.

7. The method as set forth in claim 6, further including:
   selecting at least one range of depths;
   comparing the selected range of depths with the depth determined from the second moment and sorting the first moment data in accordance with the comparing.

8. The method as set forth in claim 7 wherein at least two depth regions are selected, the comparing step compares each determined depth with the two regions and the filtering step sorts the first moment information in accordance with the comparing, first moment information from the first depth region being reconstructed into a first image representation and first moment information from the second depth region being reconstructed into a second image representation.

9. The method as set forth in claim 1 wherein the electronic data includes an indication of the energy of the radiation.

10. A diagnostic imaging apparatus comprising:
   at least one detector head including a scintillation crystal having a front face and a rear face, radiation which is received by the scintillation crystal interacting with the scintillation crystal to generate a scintillation of light, each scintillation being generated at a depth-of-interaction measured relative to the scintillation crystal faces, and opto-electrical converters being disposed adjacent a rear face of the scintillation crystal for converting the scintillations into electrical signals;
   a coordinate circuit for determining a coordinate signal indicative of the coordinates at which each interaction occurs;
   a depth circuit for determining a depth at which each interaction occurs;
   an image reconstruction system for reconstructing the coordinate signals into an electronic image representation;
   a filter circuit for selectively filtering the coordinate signals from the coordinate circuit in accordance with the depth determined by the depth circuit.

11. The apparatus as set forth in claim 10 further including:
   an operator controlled circuit for designating at least a first range of depths;
   a comparing circuit for comparing the depth from the depth circuit with the designated range of depths, the comparing circuit being connected with the filter circuit.

12. The apparatus as set forth in claim 11 wherein the filter circuit includes a bandpass filter which passes only coordinate information from interactions occurring within the selected range of depths to the image reconstruction system.

13. The apparatus as set forth in claim 11 wherein the operator controlled circuit designates a first range of depths and a second range of depths, and the filter circuit conveys the coordinate signals corresponding to interactions in the first range of depths to the first image reconstruction system and conveys coordinate signals corresponding to the second range of depths to a second image reconstruction system.

14. The apparatus as set forth in claim 10 further including:
   a second detector head, the second detector head including a scintillation crystal;
   a coincidence circuit for receiving electrical signals from the first and second detector heads to determining the occurrence of a simultaneous interaction in scintillation crystals of both detector heads; and
   a sorting circuit for sorting the coordinate signals from the coordinate circuit in accordance with whether corresponding interactions occurred simultaneously.

15. The apparatus as set forth in claim 13 further including a positron emission tomography reconstruction processor which receives the coordinate signals from events which occur simultaneously.

16. The apparatus as set forth in claim 15 wherein the filter circuit is connected between the sorting circuit and the positron emission tomographic reconstruction system.

17. The apparatus as set forth in claim 16 wherein the filter circuit is connected between the sorting circuit and the first reconstruction system such that the positron emission tomographic processor is limited to receiving coordinate information from interactions occurring in a first range of depths within the scintillation crystals and the first reconstruction system is limited to receiving coordinate information from interactions occurring in a second range of depths in the scintillation crystals.

18. The apparatus as set forth in claim 16 wherein the filter circuit is connected between the sorting circuit and the first reconstruction system.

19. The apparatus as set forth in claim 10 further including means for determining an energy of each interaction and means for selectively filtering the coordinate signals from the coordinate circuit based on the determined energy.

* * * * *